(12) United States Patent
Dittmer et al.

(10) Patent No.: US 11,493,507 B2
(45) Date of Patent: Nov. 8, 2022

(54) HIGHLY SENSITIVE IMMUNOASSAY WITH LARGE PARTICLE LABELS

(75) Inventors: Wendy Uyen Dittmer, Eindhoven (NL); Toon Hendrik Evers, Eindhoven (NL); Marco Hendrikus Hefti, Wijchen (NL); David Walterus Cornelis Dekkers, Veldhoven (NL); Michael Franciscus Wilhelmus Cornelis Martens, Helmond (NL)

(73) Assignee: Siemens Healthineers Nederland B.V., The Hague (NL)

( * ) Notice: Subject to any disclaimer, the term of this patent is extended or adjusted under 35 U.S.C. 154(b) by 420 days.

(21) Appl. No.: 13/496,023

(22) PCT Filed: Sep. 7, 2010

(86) PCT No.: PCT/IB2010/054020
§ 371 (c)(1),
(2), (4) Date: Mar. 14, 2012

(87) PCT Pub. No.: WO2011/030286
PCT Pub. Date: Mar. 17, 2011

(65) Prior Publication Data
US 2012/0171781 A1    Jul. 5, 2012

(30) Foreign Application Priority Data
Sep. 14, 2009 (EP) .................................. 09170177

(51) Int. Cl.
*G01N 33/543* (2006.01)

(52) U.S. Cl.
CPC . *G01N 33/54346* (2013.01); *G01N 33/54333* (2013.01); *G01N 2333/58* (2013.01)

(58) Field of Classification Search
CPC ........ C12Q 2563/137; C12Q 2563/149; C12Q 2563/143; G01N 27/745; G01N 33/54326;
(Continued)

(56) References Cited

U.S. PATENT DOCUMENTS

| 5,736,349 A | 4/1998 | Sasaki |
| 5,981,297 A | 11/1999 | Baselt |
| 7,879,569 B2 * | 2/2011 | Moore ..................... B82Y 5/00 |
| | | 435/7.23 |

(Continued)

FOREIGN PATENT DOCUMENTS

| AU | 758562 | * 1/2000 | ........................ 33/68 |
| EP | 1473567 A1 | 11/2004 | |

(Continued)

OTHER PUBLICATIONS

Del Ry et al., (Clinical Chem. Lab Med 2001; 39(5):446-450).*

(Continued)

*Primary Examiner* — Rebecca M Giere
*Assistant Examiner* — Xiaoyan Zou
(74) *Attorney, Agent, or Firm* — BakerHostetler

(57) ABSTRACT

An immunoassay for the detection of an analyte in a sample includes a plurality of moieties capable of binding to the analyte. Capture moieties, which are not specific for the same epitope, are bound to a solid substrate, and at least one epitope-specific detection moiety is bound to a detectable marker. The detectable marker is a large particle marker having a particle size of $\geq 50$ nm and $\leq 5000$ nm.

9 Claims, 4 Drawing Sheets

(58) Field of Classification Search
CPC .......... G01N 33/54346; G01N 33/558; G01N 33/587; G01N 2035/00544; G01N 2291/0423; G01N 2446/20; G01N 33/557; G01N 33/58; G01N 33/6893; G01N 33/74; G01N 2800/325; G01N 2800/32; G01N 2800/324; G01N 333/575; G01N 2333/475; G01N 33/53; G01N 33/5433; G01N 2333/58; C07K 14/47; C07K 14/72; C07K 14/58; C07K 16/40; C07K 14/59; A61K 38/2242; A61K 2039/505; A61K 39/395; A61K 33/54346; A61K 33/5433; A61K 2333/58

See application file for complete search history.

(56) References Cited

U.S. PATENT DOCUMENTS

| | | |
|---|---|---|
| 2004/0018577 A1 | 1/2004 | Campbell |
| 2007/0059767 A1 | 3/2007 | Karl |
| 2007/0299016 A1 | 12/2007 | Pau |
| 2008/0050749 A1 | 2/2008 | Amann-Zalan |

FOREIGN PATENT DOCUMENTS

| | | | | |
|---|---|---|---|---|
| EP | 1798504 | * | 6/2007 | ............. F26B 5/06 |
| WO | WO0045176 | * | 1/2000 | ..................... 33/68 |
| WO | 2004046727 A1 | | 6/2004 | |
| WO | 2006079998 A1 | | 8/2006 | |
| WO | 2009074933 A1 | | 6/2009 | |
| WO | 2010073182 A1 | | 7/2010 | |
| WO | WO2010073182 | * | 7/2010 | ............. G01N 33/68 |

OTHER PUBLICATIONS

Hytest publication (2005; retrieved from URL: www.hytest.fi/data_sheets/newsletters/ProBNP%20and%20Derivatives%20Newsletter.pdf).*

Figal et al., Rev Esp Cardiol. 2005;58(10):1155-61.*

Dittmer et al., Journal of Immunological Methods, 2008, 338, 40-46.*

Ademtech retrieved from http://www.ademtech.com/products.aspx?id_p=21 on Oct. 15, 2013.*

Seferian et al. (Clinical Chemistry, 2008, vol. 54:5, pp. 866-873).*

De Boer et al. (Biosensors and Bioelectronics 22 ,2007; 2366-2370).*

Dittmer, W.U. et al. "Sensitive and Rapid Immunoassay for Parathyroid Hormone using Magnetic Particle Labels and Magnetic Actuation" Journal of Immunological Methods, vol. 338, No. 1-2, pp. 40-46, Sep. 30, 2008.

Ritter M. A "Polyclonal and Monoclonal Antibodies" Methods in Moi Fcular Medicine, vol. 40, Diagnositc and Terapeutic Antibodies Edited By George Ajt and Urch CE Humana Press Inc. Totowa, NJ Aug. 2000.

Aytur T et al, "A Novel Magnetic Bioassay Platform Using a Microchip Based Sensor for Infectious Disease Diagnosis" Journal of Immunological Methods, Elsevier Science Publishers, vol. 314, Issues 1-2 Jul. 31, 2006, p. 21-29.

Collinson P.O. et al Analytical Performance of the Nterminal Pro B Type Natriuretic Peptide (NT-PROBNP) Assay on the ELECSYS TM 1010 and 2010 Analyzers,European Journal of Heart Failure, Elsevier B.V. Amsterdam,Nv vol. 6, Issue 3, Mar. 2004, p. 365-368.

Rowland A.M. et al, "A Simple Approach to Improving Sensitivity in a One-Step Monoclonal Antibody Based ELISA for Human IIBIIIA Using Multiple Conjugates" Journal of Mmunological Methods Elsevier Science Publishers BV Amsterdam, NL, vol. 151, No. Issues 1-2, Jul. 6, 1992 p. 87-95.

Human Probnp and Probnp-Derived Peptides (BNP and NT-PROBNP) Hytest Technotes, Aug. 2010.

Sagnella, "Measurement and Importance of Plasma Brain Natriuretic Peptide and Related Peptides" Ann. Clin. Biochem . vol. 38, pp. 83-93 (2001).

* cited by examiner

HIGHLY SENSITIVE IMMUNOASSAY WITH LARGE PARTICLE LABELS

FIELD OF THE INVENTION

The present invention relates to a highly sensitive immunoassay with large particle labels

BACKGROUND OF THE INVENTION

Immunoassays are widely used in health care and other fields to determine the presence or absence of specific molecules, such as proteins, hormones, DNA, RNA or enzymes.

A well-known immunoassay method used to determine the concentration of a specific target (the antigen) in a body fluid is the so-called "Enzyme linked immunoassay" (ELISA). Therein, analytes from a sample are immobilized on a solid support, and then an antibody specific to said analyte is added to the solid support, so that it can bind to the latter. The said antibody is linked to an enzyme. A substrate which can be converted by the enzyme in such way that a detectable moiety is produced, e.g. a fluorophore, is then added to the solid support. After a washing step, the solid substrate undergoes a treatment which allows detection of the detectable moiety, e.g. on a fluorescence reader. Thus, it can be determined whether or not the analyte was present in the sample.

A sandwich immunoassay comprises two antibodies that bind to different, non overlapping epitopes on the antigen. A first antibody (the capture antibody) is bound to a solid support and then the sample containing the antigen is added to allow complex formation between antigen and capture antibody. Unbound molecules are removed in a washing step, and then the labeled second antibody (detection antibody) is added and allowed to bind to the complex of capture antibody and antigen, thus forming the "sandwich". After a washing step to remove unbound detection antibodies the quantity of the target molecule is determined by measuring the amount of labeled detection antibody. A number of labeling techniques are used including fluorescence, chemiluminescence, radioactive or magnetic labels.

In most cases, two monoclonal antibodies are used that recognize different sites of the target. In another variant, a combination of a monoclonal capture antibody and an affinity-purified polyclonal detection antibody that has been raised against a different epitope on the antigen is used.

In health care many different molecules are measured to diagnose or monitor a disease. For example the Glucose content in the blood is measured to monitor diabetes. Glucose is a molecule that is present in the blood at relatively high concentration of about of several hundred μg to about 1 mg per mL, corresponding to concentrations lying in the range of about 3 to 6 millimol per mL. The measuring device is provided in form of a handheld device comprising a test strip.

In contrast thereto, other molecules, like the biomarker NT-proBNP, which is used to monitor heart failure, are present in the blood at significantly lower concentrations. In healthy patients, NT-proBNP is present in the blood at concentrations of about 20 pg-150 pg/mL, corresponding to about 24-176 picomol/mL. Values above 500 pg/mL are generally considered to be indicative for acute congestive heart failure (CHF).

Currently, measuring very low concentrations of biomarkers for the diagnosis of disease (for example, cardiovascular disease) requires laboratory analysis, large sample volumes and a time-to-result delay of between 15 minutes and several hours. Although these tests are compact benchtop tests, the relatively long turn around time and large sample volume makes them unsuitable for more demanding environments such as hospital emergency departments, physician's offices and ambulances, where small sample volumes, ease of use, speed and high sensitivity are required.

DEFINITIONS

The term "antibody", as used herein, shall refer to polyclonal and/or monoclonal antibodies of any isotype (IgA, IgD, IgE, IgG, IgM), or an antigen-binding portion thereof, including, but not limited to F(ab) and Fv fragments, single chain antibodies, chimeric antibodies and humanized antibodies.

The term "analyte", as used herein, shall refer to any molecule of which concentration or presence as such is to be determined. Examples of target molecules are molecular targets such as peptides, proteins, hormones, DNA, RNA and enzymes. The terms "analyte" and "target" are used interchangeably in the context of the present application.

The term "homologue" as used herein, shall refer to peptides or proteins substantially similar to said peptide or protein. The term "substantially similar" is well understood by the person skilled in the art. In particular, a variant may be an iso form or allele which shows amino acid exchanges compared to the amino acid sequence of the most prevalent peptide isoform in the human population. Preferably, such a substantially similar peptide has a sequence similarity to the most prevalent isoform of the peptide of at least 70%, preferably at least 80%, 85%, 90%, 95%, 97%, 98 or 99%. Substantially similar are also degradation products, e.g. proteolytic degradation products, which are still recognized by the binding moieties such as antibodies or by ligands directed against the respective full-length peptide. The term "variants" is also meant to relate to splice variants.

The term "solid substrate" as used herein, shall refer to the substrate to which the capture moieties which are not specific for the same epitope are bound. The terms "solid substrate" and "solid support" are used interchangeably in the context of the present application.

The term "binding moiety", as used herein, shall refer to epitope-specific detection moieties, or capture moieties which are not specific for the same epitope, respectively.

The term "epitope-specific detection moiety", as used herein, shall refer to at least one moiety which binds to one and the same epitope of a given target, e.g. an analyte protein.

Such epitope-specific detection moiety is for example a monoclonal antibody, an epitope-specific aptamer, an epitope-specific anticalin, an epitope-specific lectin, an epitope-specific affibody, an epitope-specific chemical ligand or an epitope-specific peptide. The terms "epitope-specific detection moiety" and detection moiety are used interchangeably in the context of the present application.

The term "capture moieties which are not specific for the same epitope", as used herein, shall refer to a collection of at least two moieties which bind to different epitopes of a given target, or to different subregions of the same epitope of a given target. Two moieties, from which one binds to amino acids 1-10 of an epitope of a given target, whereas the second binds to amino acids 2-11 of the same epitope, do thus qualify as "capture moieties which are not specific for the same epitope" in the meaning of the present invention.

Such capture moieties which are not specific for the same epitope are for example, a polyclonal antibody (which is, despite the use of the singular form, a plurality of at least two different antibodies), an affinity-purified polyclonal antibody (again, a plurality of at least two different antibodies), non epitope-specific aptamers, non epitope-specific anticalins, non epitope-specific lectins, non epitope-specific affibodies, non epitope-specific chemical ligands or non epitope-specific peptides. The terms "capture moieties which are not specific for the same epitope" and "capture moieties" are used interchangeably in the context of the present application.

SUMMARY OF THE INVENTION

It is an object of the invention to provide an immunoassay which overcomes the limitations as set forth above.

It is another object of the invention to provide an immunoassay which facilitates the use of large markers, or labels.

It is a further object of the invention to provide a method for the detection of an analyte in a sample, wherein an Immunoassay according to the invention is used. It is a still further object of the invention to provide a biosensor device capable of detecting an analyte according to the method of the present invention.

These objects are achieved by the assay the method and the biosensor device according to the independent claims.

According to the invention, an Immunoassay for the detection of an analyte in a sample is provided, said assay comprising a plurality of moieties capable of binding to said analyte, out of which a) capture moieties which are not specific for the same epitope are bound to a solid substrate, and b) at least one epitope-specific detection moiety is bound to a detectable marker, wherein the detectable marker to which to which the epitope-specific detection moiety is bound is a large particle marker having a particle size of ≥50 nm and ≤5000 nm.

It is vital that the capture moieties which are not specific for the same epitope bind to at least two different epitopes of a given target, or to different subregions of the same epitope of a given target.

The inventors have surprisingly found that the use of capture moieties which bind to different epitopes of a target is highly effective for improving the sensitivity of an immunoassay, when large particle markers are used for labeling the detection moieties, particularly in case a relatively small target is to be detected.

The inventors have found that the use of a large particle marker results in a loss of rotational freedom of the complex of epitope-specific detection moiety, target and large particle marker. Furthermore, the translational and/or diffusional speed, which is dependent on the particle radius, is also reduced for large particle markers.

Due to the bulk size of the marker the complex of epitope-specific detection moiety, target and large particle marker cannot move and rotate as fast as a complex of epitope-specific detection moiety and target having a small marker. This is detrimental in a setting where the assay time is short, as some of the capture moieties do not have enough time to couple to the target bound to the epitope-specific detection moiety carrying a large particle marker. Accordingly not all complexes of epitope-specific detection moiety, target and large particle marker will be coupled to a capture moiety and thus to the solid support. These unbound complexes will be removed in a washing step, which leads to a reduced sensitivity of the assay.

The above described effects for large labels are even more pronounced when a detection moiety with a large label is used to detect a small target, as this will further reduce the degrees of freedom of complex of epitope-specific detection moiety, target and large particle marker to move into the right position to bind to the capture moiety.

Before this background, the inventors of the present invention surprisingly found that it is extremely helpful when capture moieties which are not specific for the same epitope are used as a capture moieties. As the capture moieties which are not specific for the same epitope bind to different epitopes of the analyte, they can thus bind analytes no matter what position, or angle, they take in. This means that the loss of rotational freedom caused by the large labels carried by the detection moiety is compensated by the use of capture moieties which are not specific for the same epitope. The above described effect will be even more pronounced if one marker carries more than one detection moiety and accordingly more than one analyte is bound to one marker.

The capture moieties which are not specific for the same epitope and the detection moiety preferably bind to different sites (epitopes) of an analyte or a homologue thereof.

In one embodiment the capture moieties which are not specific for the same epitope bound to the solid support are directed to at least two different epitopes or at least two different subregions of the same epitope on the analyte. Most preferred the capture moieties which are not specific for the same epitope are directed to between ≥2 and ≤10 different epitopes or different subregions of the same epitope. Preferably the capture moieties which are not specific for the same epitope are a polyclonal antibody. In a preferred embodiment the capture moieties which are not specific for the same epitope are a sheep polyclonal antibody, and/or a goat or rabbit polyclonal antibody.

In preferred embodiment, the analyte is a cardiac hormone. More preferred, the cardiac hormone is a natriuretic peptide. The peptide may be BNP and/or NT-pro BNP. Most preferred, the peptide is human BNP and/or human NT-pro BNP.

Brain natriuretic peptides (BNP) and the related molecule NT-proBNP are substances that are released into the blood stream and are used to diagnose and monitor heart failure.

The determination of BNP and/or NT-proBNP has strict requirements in precision and high requirements for sensitivity as patient blood levels of BNP and/or NT-proBNP at several picomolar or above have important clinical consequences. Because of the urgent nature of heart failure, it is desirable to have a test that is able to deliver lab-quality results in a short time that can be used in point-of-care settings such as an emergency department or an ambulance.

The pre-pro peptide of BNP (pre-proBNP) has 134 amino acids and comprises a short signal peptide, which is enzymatically cleaved off to release the pro peptide (proBNP) a having 108 amino acids. The pro peptide is further cleaved into BNP, comprising amino acids 77-108 of proBNP and an N-terminal pro peptide (NT-proBNP). NT-proBNP is a small peptide consisting of only 76 amino acid residues having a molecular weight of about 8.5 kDa. BNP is an even smaller peptide of 32 amino acids having a molecular weight of about 3.5 kDa.

When the target is human proBNP or human NT-proBNP, the capture moieties which are not specific for the same epitope are directed to at least one epitope selected from the group consisting of amino acids residues 1-12, 1-21, 5-12, 13-27, 28-5 45, 39-50, 46-60 and/or 61-76 of HYTEST 8NT1.

Preferably the epitope-specific detection moieties are directed to at least one epitope selected from the group consisting of amino acids residues 1-10, 5-12, 11-22, 13-27, 26-32 and/or 61-76.

Particularly preferred, at least two the epitope-specific detection moieties are being used out of which one detects a BNP epitope and the other detects a NT pro BNP epitope.

The detectable marker to which the detection moiety is bound is a large particle marker. The particles may have a size between ≥50 nm and a few micrometers, more preferred between ≥50 nm and ≤5000 nm, such as between ≥250 nm and ≤5000 nm. Most preferred the particle size is between ≥500 nm and ≤1000 nm.

The terms "large particle label" or "label" and "large particle marker" or "marker" are used interchangeably in the context of the present application.

When large particle markers are used in an Immunoassay this will reduce the mobility the epitope-specific detection moieties, leading to a loss in binding efficiency of the large particle marker to the solid surface.

The reason for this unprecedented effect is that as the degree of freedom of the epitope-specific detection moieties bound to large particle markers are limited. This means that the speed of rotation of a complex consisting of a large particle marker carrying at least one epitope-specific detection moiety with a bound target is substantially restricted. This may lead to a situation in which the marker/detection moiety/target complex can not bind to an epitope-specific capture moiety, as the rotational angle of the former does not allow a binding between the capture moiety and the respective target epitope.

For this reason, the inventors have surprisingly found that it is beneficial to use capture moieties which are not specific for the same epitope, such as a polyclonal antibody. The latter allows binding of the marker/detection moiety/target complex no matter what rotational angle the latter has, and thus facilitates the binding of a marker/detection moiety/target complex the rotational degree of freedom of which is reduced due to large marker size.

In the context of the present invention, it is desirable to use capture moieties which are not specific for the same epitope when a large particle marker is used, as the capture moieties which are not specific for the same epitope enhance the sensitivity of an Immunoassay by improving the binding efficiency of the large particle marker to the solid surface.

In another preferred embodiment of the Immunoassay according to the invention the detectable marker to which the epitope-specific detection moiety is bound may be an optical or a non-optical marker. Preferably, the optical marker is at least one selected from the group consisting of light scattering markers, enzymatic markers, fluorescent markers, chromophoric groups, electroluminescent markers, chemiluminescent markers, phosphorescent markers, reflecting markers and/or radioactive markers.

Fluorescent markers include fluorescein dyes, such as 5-(and 6-) carboxy-4',5'-dichloro-2',7'-dimethoxyfluorescein, 5-carboxy-2',4',5',7'-tetrachlorofluorescein and 5 carboxyfluorescein, rhodamine dyes such as 5-(and 6-) carboxy rhodamine, 6-carboxytetramethyl rhodamine and 6-carboxyrhodamine X, phthalocyanines such as methyl, nitrosyl, sulphonyl and amino phthalocyanines, azo dyes, azomethines, cyanines and xanthines such as the methyl, nitro, sulphano and amino derivatives, and succinylfluoresceins. Other suitable labels are fluorophores from the group of cyanine dimers and monomers, such as TOTO, YOYO, TO-PRO, Cy3, Cy5, Cy5.5, Cy7 etc., or dyes such as LCRed 705 may be used as the fluorescent marker. Other fluorescent markers are fluorescent proteins, like GFP and the like.

A light scattering marker is preferably used in case FTIR (Frustrated total internal reflection) is used as a detection technique, the latter being described below. Light scattering occurs, for example, when a beam of light passes through a colloidal dispersion, as the particles or droplets scatter some of the light in all directions. When the particles are very small compared to the wavelength of the incident light, than the intensity of the scattered light is uniform in all directions (Rayleigh scattering). For larger particles (above approximately 250 nm diameter), the intensity is angle dependent (Mie scattering).

Such light scattering marker is, for example, a bead with a diameter of greater than 250 nm, so that it can scatter incoming light in an angel dependent manner. These beads are opaque, in such way that they do not transmit light. They can, for example, be made of dyed plastics, metal and the like.

A large label having a size of greater than 250 nm is preferred when a light scattering marker is used. As mentioned above the use of a large marker will lead to a reduced freedom of rotation of the epitope-specific detection moieties bound to the large particle markers.

In a preferred embodiment, the detectable marker is a magnetic marker, or a marker linked to a magnetic particle. The use of magnetic markers as detectable markers is preferred as they enable to speed up the reaction kinetics by use of magnetic actuation, thus reducing the assay time. In addition the use of magnetic markers facilitates improving the sensitivity of the assay by using pulsed magnetic actuation. Moreover, the use of magnetic markers enables binding of the detection moiety-target complex to the solid support. Furthermore the use of magnetic labels facilitates removal of any label, bound or unbound to the detection moiety, that is not bound to the sensor surface via a magnetic field. This embodiment abolishes the need for additional washing steps to identify specific signal versus background binding.

Accordingly the detectable marker can also be used as a handling agent facilitating the binding of the detection moiety-target complex to the solid support. Preferably the detectable marker thus double-acts as a handling agent.

When the magnetic marker is used as detectable marker, the magnetic marker may be detected optically or magnetically. Preferably the magnetic marker is optically detected, preferably by frustrated total internal reflection (FTIR).

The nature of the magnetic marker, or particle, used in the context of the present invention is not critical. Suitable magnetic labels include completely inorganic labels and labels which comprise a mixture of an inorganic and an organic material (e.g. a polymer). Magnetic labels are commercially available from e.g. Dynal, Estapor, Seradyn and are widely used in biological analysis that are available from several diagnostic companies.

Attachment of the magnetic label to the epitope-specific detection moiety can be performed by methods described in the art. For instance, the magnetic label may carry one or more functional groups such as hydroxyl, carboxyl, aldehyde or amino groups. These may in general be provided, for example, by treating uncoated monodisperse, superparamagnetic labels, to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. The coupling of an epitope-specific detection moiety to a particle can be irreversible but can also be reversible by the use of a linker molecule for the crosslinking between label and epitope-specific detection moiety. Examples of such linkers include peptides with a certain proteolytic recognition site, oligonucleotide sequences with a recognition site for a certain restriction enzyme, binding partners such as streptavdin/biotin, or chemical reversible crosslinking groups as those comprising a reducible disulfide group. A variety of reversible crosslinking groups can be obtained from Pierce Biotechnology Inc. (Rockford, Ill., USA).

The non-optical label may be an acoustic label.

In a further preferred embodiment of the Immunoassay according to the invention the analyte is a small peptide or protein. As used herein, the term "small peptide or protein" refers to a peptide or protein with ≥20 and ≤180 amino acid residues. BNP has, for example, 32 amino acid residues (3.47 kD), while NT-proBNP has 76 amino acid residues (8.46 kD). Likewise, the term "small peptide or protein" refers to a peptide or protein with a molecular weight of ≥2 and ≤17 kDa.

It is important for the understanding of the present invention that the above described effects for large labels are even more pronounced, when a detection moiety with a large label is used to detect a small target. When the combination of large marker and small target is used, the degrees of rotational freedom will be limited more dramatically than in case a large marker is used to detect a large target. Accordingly the detection moiety/target complex will require more time to move into the right position to bind to the capture moiety and thus to the solid support. Thus even less target proteins will be coupled to the solid support in a setting where a short assay time is used. These unbound target proteins will be removed in a washing step, which leads to a reduced sensitivity of the assay. This will be detrimental in point-of-care settings, where small sample volumes, ease of use, speed and high sensitivity are required.

Preferably the peptide is a cardiac hormone. More preferred the cardiac hormone is a natriuretic peptide. The peptide may be BNP and/or NT-pro BNP. Particularly the peptide is human BNP and/or human NT-pro BNP.

As mentioned above, NT-proBNP is a small peptide consisting of only 76 amino acid residues having a molecular weight of about 8.5 kDa. BNP is an even smaller peptide of 32 amino acids having a molecular weight of about 3.5 kDa.

This property is highly disadvantageous when NT-proBNP or BNP containing large particles are required to bind to a solid sensor surface through this small peptide for detection. Like described above, small target proteins, such as NT-proBNP and/or BNP, require more time to move into the right position to bind to the capture moiety and thus to the solid support when coupled to a large marker, as the degrees of rotational freedom for the detection moiety-target complex are highly limited in this situation.

Before this background, the inventors have surprisingly found that it is highly beneficial to use capture moieties which are not specific for the same epitope, such as a polyclonal antibody, for the determination of NT-proBNP. The use of capture moieties which are not specific for the same epitope allow for binding of the marker/detection moiety/target complex no matter what rotational angle the latter has, and thus facilitates the binding of a marker/detection moiety/target complex the rotational degree of freedom of which is reduced due to the large size of the marker and the small size of NT-proBNP.

In one embodiment the analyte is contained in a sample. The term "sample" is used in a broad sense herein and is intended to include a wide range of biological materials as well as compositions derived or extracted from such biological materials. Preferably the analyte is contained in a body fluid or tissue sample, and the amount of the analyte in the sample is measured.

In a preferred embodiment the analyte can be measured in tissue, cell, and body fluid samples, i.e. preferably in vitro. Preferably, the analyte of interest is measured in a body fluid sample. A tissue sample according to the present invention refers to any kind of tissue obtained from the dead or alive human or animal body. Tissue samples can be obtained by any method known to the person skilled in the art, for example by biopsy or curettage.

Body fluids according to the present invention may include blood, blood serum, blood plasma, lymph, cerebral liquor, saliva, mucus, semen, stool, spinal fluid, urine and/or sputum or any fraction thereof. Particularly, the body fluid is at least one selected from the group consisting of blood, blood serum, blood plasma, urine, salvia and/or sputum. Samples of body fluids can be obtained by any method known in the art. Exemplary samples include whole blood, red blood cells, white blood cells, buffy coat, hair, nails and cuticle material, swabs, including but not limited to buccal swabs, throat swabs, vaginal swabs, urethral swabs, cervical swabs, rectal swabs, lesion swabs, abscess swabs, nasopharyngeal swabs, nasal swabs and the like, lymphatic fluid, amniotic fluid, cerebrospinal fluid, peritoneal effusions, pleural effusions, fluid from cysts, synovial fluid, vitreous humor, aqueous humor, bursa fluid, eye washes, eye aspirates, plasma, serum, pulmonary lavage, lung aspirates, biopsy material of any tissue in the body. The skilled artisan will appreciate that lysates, extracts, or material obtained from any of the above exemplary biological samples are also considered as samples. Tissue culture cells, including explanted material, primary cells, secondary cell lines, and the like, as well as lysates, extracts, supernatants or materials obtained from any cells, tissues or organs, are also within the meaning of the term biological sample as used herein. These lists are not intended to be exhaustive.

In particular embodiments of the invention, the sample is pre-treated to facilitate the detection of the sample with the detection method. For instance, typically a pre treatment of the sample resulting in a semi-isolation or isolation of the target is envisaged. Many methods and kits are available for pre-treating samples of various types. Mostly preferred the sample is blood.

The epitope-specific detection moiety may be a monoclonal antibody, an affinity purified polyclonal antibody, an epitope-specific aptamer, an epitope-specific anticalin, an epitope-specific lectin, an epitope-specific affibody, an epitope-specific chemical ligand or an epitope-specific peptide. Most preferred the epitope-specific detection moiety is a monoclonal antibody.

By using detection moieties that all bind to the same epitope, the formation of complexes in the medium can be avoided. When large particle labels are used, more than one detection moiety can be bound to one label particle. In case the detection moieties would bind to different epitopes, it can occur that different detection moiety-label complexes bind to more than one target. This may led to the formation of large complexes which eventually might precipitate. Detection moieties that are specific to the same epitope or subregions of the same epitope avoid that problem as they always bind to the same epitope.

The detection moiety may be linked to the large particle label in any suitable way. This linking may be done by any suitable method such as covalent linking or non-covalent linking or adsorption. The Ademtech protocol, known for a person skilled in the art, can be used for linking magnetic labels to the epitope-specific detection moiety. In this protocol, a detection moiety, such as a monoclonal antibody at a concentration of for example 20 ug antibody/mg magnetic label is coupled to 25 carboxylated magnetic labels in the presence of EDC (1-Ethyl-3-(3-dimethylaminopropyl)-carbodiimide).

When the target is human proBNP or human NT-proBNP, the capture moieties which are not specific for the same epitope are directed to at least one epitope selected from the group consisting of amino acids residues 1-12, 1-21, 5-12, 13-27, 28-45, 39-50, 46-60 and/or 61-76 of HYTEST 8NT1.

Preferably the epitope-specific detection moieties are directed to at least one epitope selected from the group consisting of amino acids residues 1-10, 5-12, 11-22, 13-27, 26-32 and/or 61-76.

Particularly preferred, at least two epitope-specific detection moieties are being used out of which one detects a BNP epitope and the other detects a NT pro BNP epitope.

In a preferred embodiment the solid substrate has essentially a shape selected from the group consisting of beads, strips, slides and/or chips. Furthermore, the surface can be flat, curved, porous or structured, e.g. in order to achieve a structured optical surface for enhanced sensitivity when using optical detection techniques.

The solid substrate may be the surface of a sensing device. Typically, the surface of the sensing device is a solid, uniform surface. The surface can be a sensor surface, i.e. a surface which is involved in detection. Alternatively, the sensor can be located in the vicinity e.g. under the surface of the sensing device, allowing detection of labels present close to the detection surface.

The sensing device may be any sensing device suitable for detecting a label. Suitable sensing devices may be non-optical sensing devices or optical sensing devices. The non-optical sensing device may be capable of detecting a non-optical signal such as, but not limited, to a magnetic signal, magnetoresistance and/or a Hall effect. The optical sensing device may be capable of detecting an optical signal such as reflection, absorption, scattering, fluorescence, radioactivity, chemiluminescence, RAMAN and/or FTIR.

Frustrated total internal reflection is a phenomenon which occurs in cases wherein an evanescent wave extends across a separating medium into a region occupied by a higher index of refraction material, energy may flow across the boundary. This phenomenon is similar to quantum mechanical tunneling or barrier penetration. When transmission across the boundary occurs in this manner, the "total internal reflection" is no longer total since the transmitted wave comes at the expense of the internally reflected one.

In practise, a light beam is directed to a glass slide, where total reflection occurs. However, part of the light enters the glass slide and creates an evanescent field. Scattering markers which are close to the glass slide cause light scattering within the evanescent field and are thus detectable with a respective device, e.g, a CCD camera.

The applicant has, in prior inventions, for the first time disclosed the use of a frustrated total internal reflection technique in diagnostic assays. It has turned out that this method provides high sensitivity, short assay times and requires only small sample volumes. This is an advantage in point-of-care settings where speed and high sensitivity are required.

In particular embodiments detection means are capable of detecting an non-optical signal such as an acoustical signal (quartz crystal microbalance (QCM), surface acoustic waves (SAW) or Bulk Acoustic Wave (BAW) etc.). Such acoustic signals may be generated by vesicles such as liposomes, micelles, or bubbles. Such vesicles may be filled with a liquid, a gas, a gaseous precursor, and/or a solid or solute material.

Depending on the nature of the signal to be detected, the detection surface can be an integral part of the detection means (sensor surface) or can allow the detection of the presence of labels on its surface.

In one example, radioactive labels, such as e.g. luminescent or fluorescent labels, are embedded in or attached to the labels that are used. Excitation of the fluorescent labels can be done using an irradiation source, such as for example via focused laser beam or via evanescent field excitation allowing optical detection of such labels. Detection can be done in any suitable way, such as for example using confocal detection or using a high-NA lens. The use of fluorescent labels enables multiplexing by using different fluorophores, which differ in excitation and/or emission wavelengths.

Optical detection can be done also by Surface-Enhanced Resonance Raman spectroscopy (SERRS). SERRS is an ultra-sensitive method for detection of molecules or species by adsorption of the molecule or species that is optically labeled on colloidal labels, e.g. silver particles. The optical label is a suitable dye molecule (such as Rhodamine) causing plasmon and dye resonance when the colloidal particles cluster in a controlled way. It is known that for example magnetic labels exist with a metallic coating. If a target, such as for example an antigen (to which the binding moieties, i.e. antibodies, bind) is coupled to such silver-coated magnetic label, while the target is also coupled to a suitable dye, target-specific binding moieties will lead to linking of the dye to the silver-coated magnetic labels. Magnetic actuation will lead to cluster/pillar formation which will lead to dye resonance. SERRS can be detected after actuation to a non-binding sensor surface in an evanescent field. In such a set-up, binding moiety detection can be done in a single chamber omitting fluid wash steps since the detection is surface specific and not disturbed by unbound dyes from solution. In another example, a magnetic sensor may be used, such as for example a Hall sensor, a magnetoresistive sensor such as for example an GMR, TMR or AMR sensor. In a particular example, the magnetic sensing may take advantage of the fact that a particular frequency may be used for the applied AC magnetic field. In the low frequency regime, i.e. at frequencies e.g. below 100 Hz, the 1/f noise of the magnetic sensor element dominates. 1/f noise is caused by point-to-point fluctuations of the current and is proportional to the inverse of the frequency. In magnetoresistive sensors, 1/f noise originates from magnetic fluctuations in the free layer. When the frequency of the generated AC magnetic field is 100 Hz or above, the dominating 1/f noise is significantly reduced compared to the prior art, resulting in an improved signal to noise ratio (SNR). It is advantageous when the frequency of the AC magnetic field is further increased to a value where the thermal white (Nyquist) noise level becomes dominant over the 1/f noise level. Above a certain corner frequency fc» 50 kHz the thermal white noise of GMR sensors becomes dominant. The white-noise level limits the theoretically achievable detection limit.

As mentioned above the detection of magnetic labels at a detection surface can be ensured by any direct or indirect method known in the art. Particular detection methods are based on the magnetic properties of the label such as GMR or on optical properties of the magnetic labels, such as detection with frustrated total internal reflection (FTIR). Miniaturised GMR sensor chips, integrated in disposable flow-cell cartridges, are suitable for performing the methods of the present invention, and can detect a label density of three 300 nm labels on a 1500 µm² chip surface.

In another preferred embodiment the solid substrate comprises at least one material selected from the group consisting of latex, plastic, gold, silicon, silicon nitride and/or glass.

The capture moieties which are not specific for the same epitope may be linked to the solid support in any suitable way. This linking may be done by any suitable method such as covalent linking or non-covalent linking or adsorption. For example the capture moieties which are not specific for the same epitope may be bound to the solid support by inkjet printing, microcontact printing, immersion coating (in a bulk solution) and/or drop coating (from a nano or micropipette).

In an embodiment of the invention, the epitope-specific detection moiety bound to the magnetic label and the capture moieties which are not specific for the same epitope bound to the sensor surface are present within a cartridge. As the reagents for the assay are already present within the cartridge, the user only needs to add the sample fluid via the sample inlet, which redisperses the reagents and labels to produce the intended buffer conditions. The dry reagents preferably include the buffer components necessary for the assay and the magnetic labels with the epitope-specific detection moiety. The components of the dry reagents can be deposited and dried individually at different location in the cartridge or together at the same location. The reagents can be deposited via several drying techniques including lyophilization. Lyophilization prevents the formation of crystals and allows the reagents to be dried to an amorphous glassy state that is readily redispersed upon the addition of a fluid. The cartridge preferably is suitable detection of the large particle label. Mostly preferred the cartridge is suitable for optical detection of the magnetic labels.

In another embodiment of the present invention, a method for the detection of analytes in a sample is provided wherein an immunoassay according to the invention is used.

Preferably, the detectable marker is detected with an optical or non-optical detection method. In a further preferred embodiment the detectable marker is detected with at least one method selected from the group consisting of frustrated total internal reflection (FTIR), luminescence measurement, fluorescence measurement, absorbance measurement, weight measurement, and/or glass radioactivity measurement.

Furthermore, it is preferred that the detectable marker is a magnetic marker, and/or that the detectable marker is detected with FTIR.

In particular embodiments of the method described in the present invention, the optimization of target-binding moiety interaction is achieved by magnetic actuation; applying a magnetic field directed towards the detection surface and/or pulsed magnetic actuation forces to the magnetic labels carrying the epitope-specific detection moiety during the assay to ensure optimized contact with the detection surface. Magnetic labels can be manipulated in different ways to optimise contact with the immobilized binding moieties. In particular embodiments, magnetic actuation in the assay is performed as follows.

In a first step, the labels with the epitope-specific detection moiety are rapidly attracted to the sensor surface in a "collection" step. This is ensured by applying a magnetic field in the direction of the sensor surface. In particular embodiments the magnetic field ensures that the magnetic labels have reached the sensor surface, for instance such as to reach at least 50%, 75% or 90% of monolayer formation on the surface, preferably 100% monolayer formation. In a second step, the magnetic forces are removed and the labels are allowed to move over the surface with essentially unhindered translational as well as rotational degrees of freedom. After a certain time diffusion occurs and, in particular embodiments it is envisaged that the oriented magnetic field of the first step is once again applied. These steps can be repeated several times to ensure that all magnetic labels with the target bound to the epitope-specific detection moieties are bound to the non epitope-specific detection moieties on the detection surface. By this alternation of on/off of the magnetic field, pulsed actuation is obtained.

In alternative embodiments of the magnetic actuation conditions envisaged herein, the rotation and translation at the detection surface is not merely a result of passive diffusion in the absence of a magnetic field, but is actively ensured by the application of one or more magnetic fields which ensure the movement of magnetic labels over the detection surface.

In particular embodiments the magnetic force enabling the movement of magnetic labels over the detection surface is ensured by pulsed actuation of the labels. This can involve e.g. alternating the direction of a magnetic field perpendicular to the detection surface or parallel to the detection surface or a combination of different fields with different orientations. The time and duration of each pulse is designed based on the label size so as to optimally allow the label to undergo at least one full rotation over its axis over the binding surface. In particular embodiments, the actuation forces are essentially perpendicular to the surface as strong forces parallel with the sensor surface can remove specifically bound magnetic labels.

In methods described herein it is optionally envisaged that, after the contacting of the magnetic labels with the detection surface through magnetic actuation, a magnetic force is applied directing the labels away from the detection surface to ensure the removal of unbound labels. In this way additional washing steps for removal of the magnetic label are no longer necessary.

It has been found that methods involving pulsed actuation alternated with translational and rotational movement of magnetic labels on the detection surface are significantly more efficient than methods which involve only a constant magnetic force attracting the labels to the detection surface. The pulsed actuation also reduces the probability that labels irreversibly aggregate as the amount of time that the labels are in contact with one another is also reduced.

A preferred actuation scheme consists of about 1 minute incubation of the sample with the cartridge and magnetic labels followed by about 4 minute pulsed actuation and about 10 second label removal with a top coil.

The Immunoassay may be carried out in any assay format that is suitable. For example the immunoassay may be carried out as a sandwich assay, a competitive immunoassay or as an inhibition assay.

The assay may also be carried out as competitive assay format in which the most prevalent isoform of the peptide or protein compete with homologues of said peptide or protein that are immobilized on the large particle label for polyclonal binding sites on the solid support. When NT-proBNP is used as target, NT-pro BNP compete with NT-pro BNP-homologues that are immobilized on the large particle label for polyclonal binding sites on the solid support.

In a preferred embodiment the assay is carried out in the 1-step format comprising the steps of:

a) adding magnetic particles conjugated to the detection moieties to the sample suspected to contain the analyte, b) exposing the sample with particles to the sensor surface containing the capture moieties and c) permitting complex formation of detection moieties, analyte and capture moieties.

d) removing unbound particles and e) detecting the number of bound detection moieties In another aspect the invention provides a method for the detection of analytes in a sample, wherein an Immunoassay according to the invention is used. The level or concentration of a suitable analyte can indicate the presence or absence of a condition, disease, or complication, and thus allow diagnosis and/or monitoring of said condition, disease or complication. In particular the method is used to diagnose and/or monitor heart failure.

The assay times may be less than ≤5 Minutes. The sample volumes may be smaller than ≤30 μL, such as for example between ≥1 μL and ≤30 μL.

The label, or marker, which is used for these purposes is a label as set forth above. Preferably the marker is a magnetic label. These magnetic labels have, however, a relatively large size, preferably in the range of ≥50 nm and ≤5000 nm.

Furthermore, the invention provides a biosensor device capable of detecting an analyte in a sample according to the method according to the invention. Such biosensor is optimally suited for mobile use, e.g. as a handheld device, and allows quick detection of analytes which are abundant only in small concentrations.

In a further aspect the invention provides a kit of parts suitable for detecting an analyte in a sample, comprising a) capture moieties which are not specific for the same epitope bound to a solid substrate, and b) an epitope-specific detection moiety bound to a detectable marker, wherein the detectable marker to which the epitope-specific detection moiety is bound is a large particle marker having a particle size of ≥50 nm and ≤5000 nm.

It should be clear that the preferred embodiments set forth in connection with the Immunoassay according to the invention are also applicable with the kit of parts mentioned above.

BRIEF DESCRIPTION OF THE DRAWINGS

These and other aspects of the invention will be apparent from and elucidated with reference to the embodiments described hereinafter.

In the drawings.

The detectable marker 16 to which the epitope-specific detection moiety 15 is bound is a large particle marker having a particle size of ≥50 nm and ≤5000 nm. It can be an optical or non-optical marker, for example a light scattering marker. Furthermore, the marker can serve as a handling agent, for example if it has magnetic properties. Due to the large size of the marker, the marker/detection moiety/analyte complex has a limited rotational degree of freedom, as symbolized by the dotted arrow. This is however accounted for by the use of capture moieties which are not specific for the same epitope comprising at the least two moieties 11, 12 which are not specific for the same epitope of the analyte 13. Therefore, the marker/detection moiety/target complex can bind to the substrate even if it has not a fixed rotational angle with respect to the substrate. This increases speed and sensitivity of the assay, and makes it thus useful for appliances wherein a) large markers are being used (like light scattering markers)

b) small analytes are being detected (like NT-proBNP or BNP)

c) analysis has to be done quickly (as required in emergency devices, particularly handheld devices), and d) the analyte is abundant only in small quantities (pg/ml–ng/ml scale, as it is the case for NT-proBNP and BNP)

Figure 1:
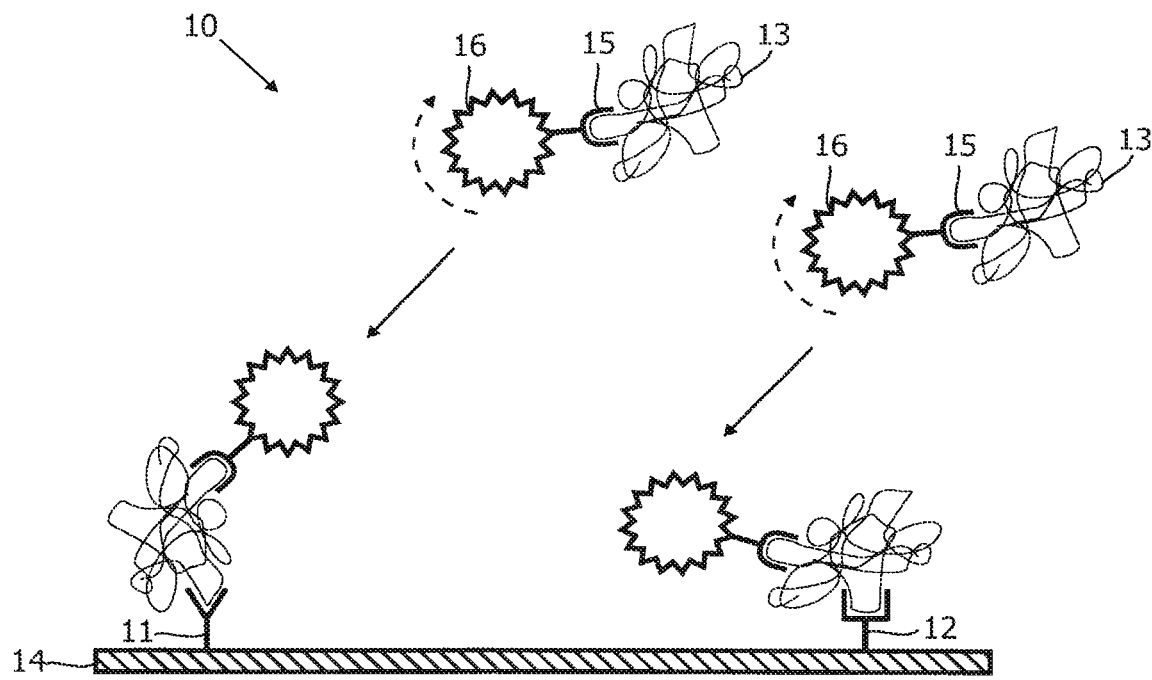
FIG. 1 shows the principle set forth in an immunoassay 10 according to the invention. The assay comprises capture moieties comprising at least two moieties 11, 12 which are not specific for the same epitope of an analyte 13. The capture moieties are bound to a solid substrate 14. The assay further comprises at least one epitope-specific detection moiety 15 which is bound to a detectable marker 16. The two moieties 11, 12 are not specific for the same epitope of an analyte but belong to the same polyclonal antibody. The epitope-specific detection moiety is a monoclonal antibody.
Figure 2:
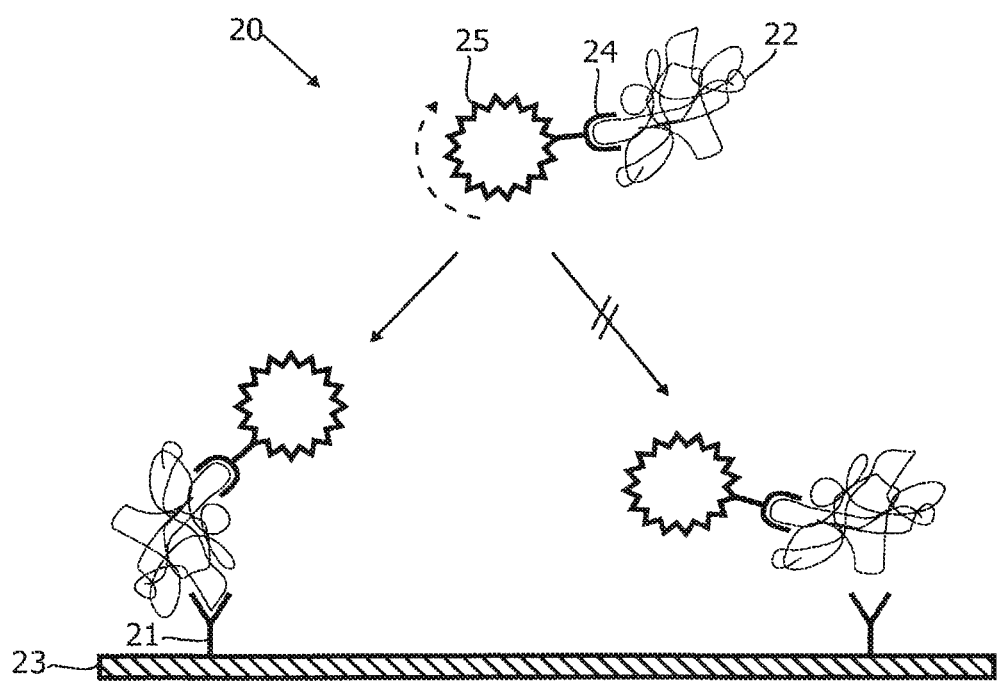

FIG. 2 shows the problem which occurs in immunoassays according to the state of the art. Here, the immunoassay 20 comprises only one type of epitope specific capture moiety 21, namely a monoclonal antibody specific for an epitope of an analyte 22. The monoclonal antibody 21 is bound to a solid substrate 23. The assay further comprises at least one epitope-specific detection moiety 24 which is bound to a detectable marker 25. The complex can only bind to the epitope specific capture moiety 21 if it has the right rotational angle (see left portion of FIG. 2). Due to the large size of the marker, the marker/detection moiety/analyte complex has a limited rotational degree of freedom. Therefore, in case the rotational angle of marker/detection moiety/analyte complex is not correct, the complex cannot bind to the solid substrate 23. This reduces speed and sensitivity of the assay, particularly in cases when at least one of the conditions a)-d) as described above are met.

Figure 3A:
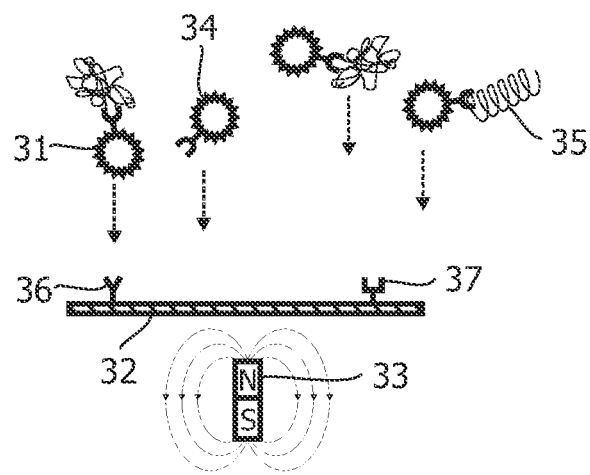
Figure 3B:
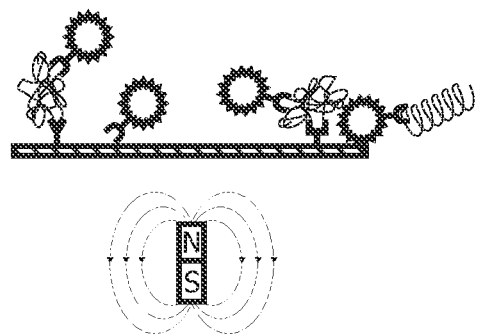
Figure 3C:
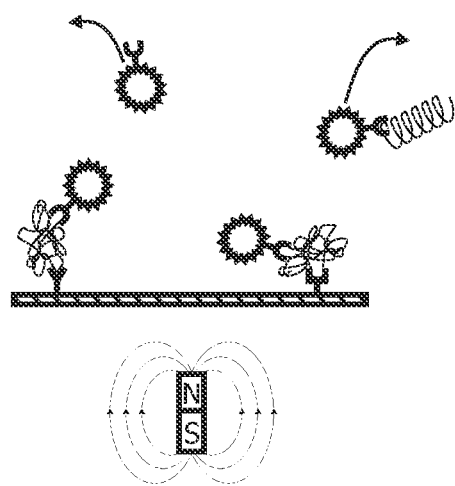

FIG. 3 gives an overview over the magnetic approach according to a preferred embodiment of the invention. In this case, the marker/detection moiety/analyte complex has magnetic properties, either because of the fact that the marker is magnetic (it then double-acts as a marker and a handling agent) or because a magnetic agent is added to the complex.

In step a), marker/detection moiety/analyte complexes 31 are attracted to the solid substrate 32 by a magnetic field applied by a magnetic actuator 33. Furthermore, marker/detection moieties 34 not carrying an analyte are attracted to the solid substrate as well as marker/detection moieties 35 which have bound, e.g. by unspecific binding, a different target. The solid substrate has capture moieties comprising at least two moieties 36, 37 which are not specific for the same epitope of the analyte bound in the marker/detection moiety/analyte complexes 31.

In step b), the marker/detection moiety/target complexes 31 bind to moieties 36, 37 even if they have different rotational angles with respect to the substrate. The free marker/detection moieties 34 and the marker/detection moieties 35 having bound a different target, bind to the solid substrate as well due to magnetic forces.

In step c), the magnetic field of the magnetic actuator is reversed, thus repelling all magnetic agents not specifically bound to the solid substrate. Therefore, the free marker/detection moieties 34 and the marker/detection moieties 35 having bound a different target are released, while the marker/detection moiety/target complexes 31 specifically bound to the substrate are retained, and can then be detected, e.g. by the FTIR technique.

Figure 4A:
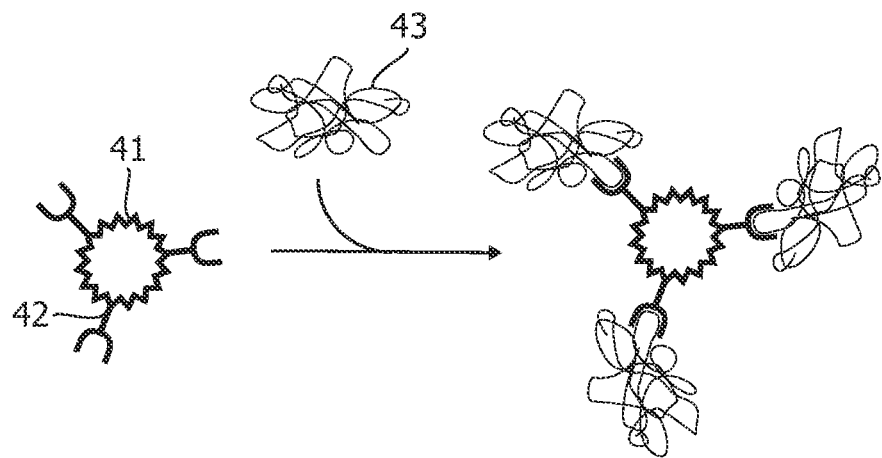

FIG. 4a shows that each marker 41 can carry more than one epitope specific detection moiety 42, e.g. monoclonal antibodies. This can lead to marker/detection moiety/analyte complexes which carry more than one analyte 43.

Figure 4B:
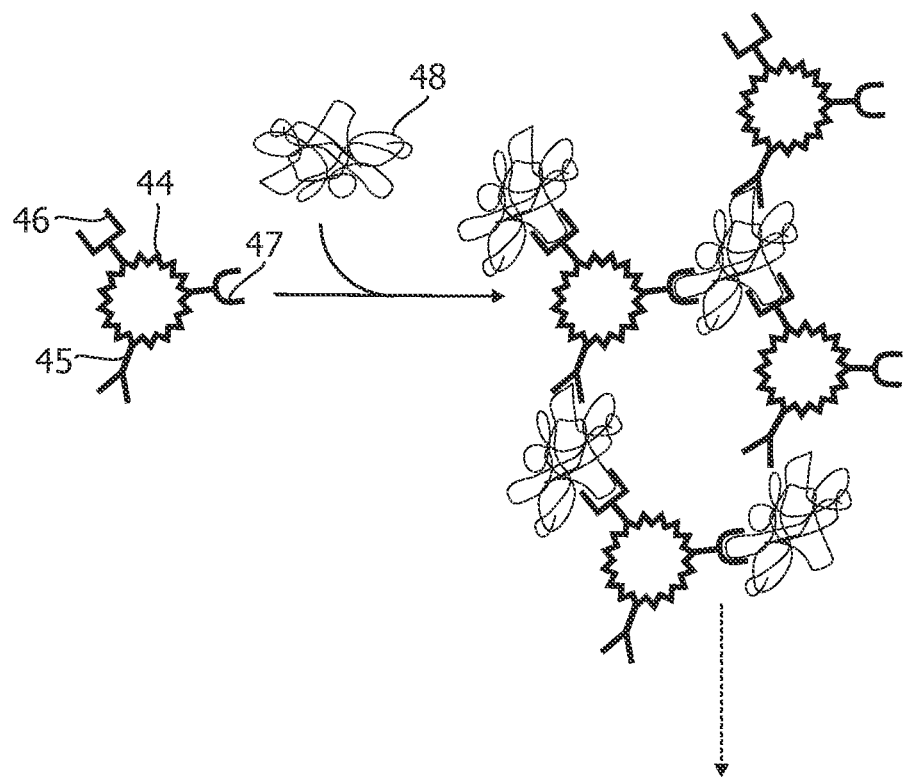

FIG. 4b shows what can happen if a marker 44 carries more than one detection moiety, wherein each moiety 45, 46, 47 binds to a different epitope of the analyte, e.g. polyclonal antibodies. This can lead to the formation of large complexes which, later on, precipitate, as symbolized by the dotted arrow. Therefore, it is preferred, in the present invention, to use epitope specific detection moieties, like monoclonal antibodies.

Figure 5:
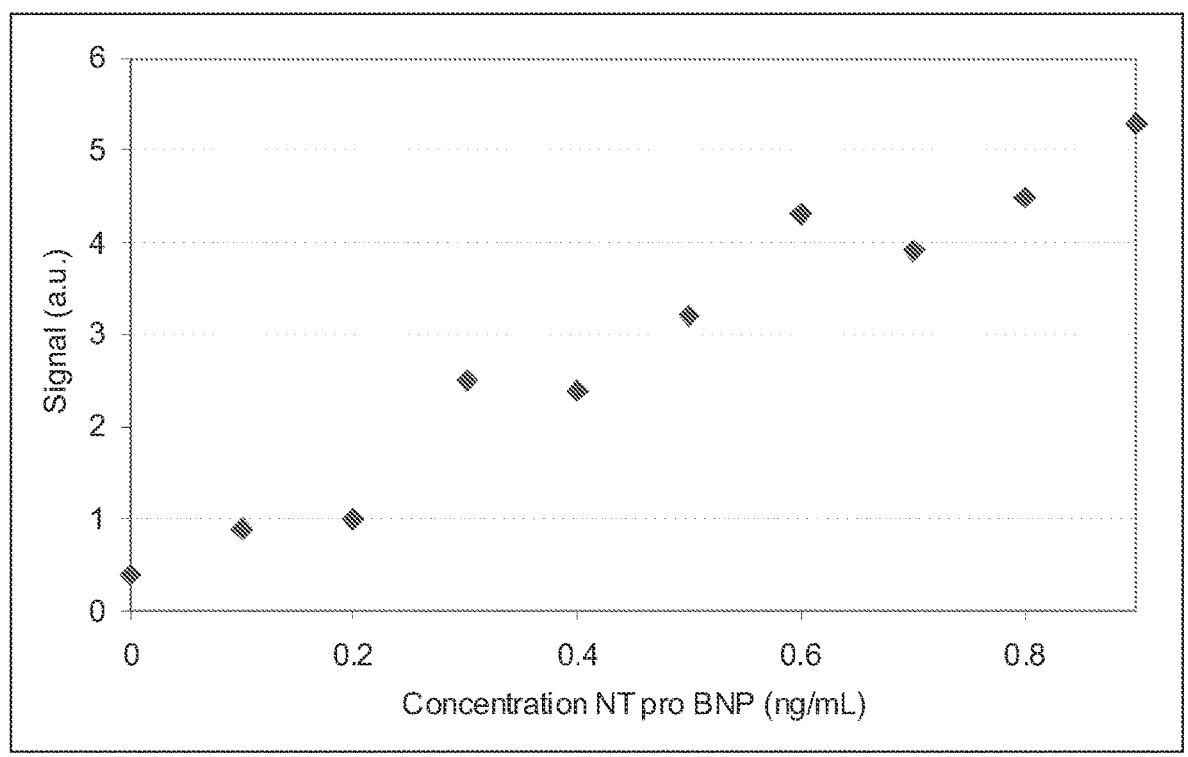

FIG. 5 shows a dose response curve for NT-pro BNP using a sheep polyclonal NT-pro BNP antibody directed to epitope 1-21 of NT-pro BNP as capture moiety. The latter are, according to the definition of the present invention, not specific for the same epitope, as they bind to different subregions of the same epitope of the given target. Measurement took place with the Frustrated Internal Total Reflection technique as described in the experimental description below. As can be seen, speed and sensitivity of the approach are exceptional. Fractional nanogram concentrations of NT-pro BNP can be detected after an incubation protocol of 4 minute pulsed magnetic actuation and 10 s magnetic marker removal.

DETAILED DESCRIPTION OF EMBODIMENTS

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

EXAMPLES

Example 1

Detection of NT-proBNP Using a Magnetic Label
1. Materials
polyclonal NT-proBNP antibody directed to epitope 1-21 of NT-proBNP
NT-pro BNP standards (Hytest 8NT1)
500 nm magnetic particles coated with 15C4 Hytest MAb antibody
2. Method
Polyclonal NT-pro BNP sheep antibody directed to epitope 1-21 was a polyclonal antibody that has been inkjet printed on to surface of a polymer biochip at a concentration of 150 ug/mL antibody in PBS. Iron oxide particles having a diameter of 500 nm covered with a particle coating from Ademtech SA functionalized with a solution of 40 ug 15C4 Hytest MAb antibody/mg magnetic particle were diluted in assay buffer. NT-pro BNP standards (Hytest 8NT1) were diluted in assay buffer. The magnetic label and NT-pro BNP solutions were diluted 1:1 and 1 μL was exposed to the sensor surface. Measurement took place with the Frustrated Internal Total Reflection technique.

Magnetic nanoparticles at the sensor surface were detected with an evanescent field created by a collimated beam of LED light with a wavelength of 625 nm at an incident angle of 70° with respect to the normal, i.e. at an angle of 20° with respect to the sensor surface. The reflected light passed through an imaging lens (f=7.5 mm, Anteryon) onto a CCD camera (Marlin F080B/C, Allied Vision Technologies). The signal due to the binding of nanoparticles to the sensor surface was calculated for each spot, averaging over an area of 20 pixels×20 pixels. The signal was determined by relating the reflected light intensity to the measured light intensity prior to the binding of nanoparticles.

An actuation protocol consisting of 4 minute pulsed actuation and 10 s label removal with a top coil was used. The solution was incubated for 30 s prior to insertion into the cartridge to allow particles to bind NT-pro BNP. After insertion of approximately 10 μL of fluid into the cartridge, the particles were attracted towards the sensor surface for 225 s while the field was alternatingly switched ($3 \cdot 10^4$ A/m). This results in the binding of particles containing NT-pro BNP to the surface containing anti-NT-pro BNP antibodies. In the final step, the lower magnet was turned off and the upper magnet was powered ($2 \cdot 10^4$ A/m) to pull the unbound particles away from the sensor surface. The total assay time was approximately 5 minutes. Results are shown in FIG. 5.

The invention claimed is:

1. An immunoassay method for detection of a target analyte human NT proBNP and human BNP in a sample, wherein the target analyte is human NT-proBNP or human BNP, said immunoassay method comprising:
adding the sample to assay reagents comprising
(a) capture moieties, which are not specific for a same epitope on the target analyte, bound to a solid substrate, wherein a first capture moiety of the capture moieties is specific for a first epitope of the target analyte, and a second capture moiety of the capture moieties is specific for a second epitope of the target analyte that is different from the first epitope, and
wherein the capture moieties are selected from the group consisting of a polyclonal antibody, an affinity-purified polyclonal antibody, non epitope-specific aptamers, non epitope-specific anticalins, non epitope-specific lectins, non epitope-specific affibodies, non epitope-specific chemical ligands, and non epitope-specific peptides, and
(b) a magnetic marker bound to at least one human-NT-proBNP-epitope-specific detection moiety or at least one human BNP-epitope specific detection moiety, wherein the human-NT-proBNP-epitope-specific detection moiety and the human BNP-epitope specific detection moiety are monoclonal antibodies, wherein the magnetic marker is a large particle marker having a particle size of >50 nm and less than or equal to 5000 nm; and
detecting optically or magnetically the magnetic marker bound to the solid substrate;
wherein the immunoassay method has a lower detection limit of NT-proBNP of 0.2 ng/ml.

2. The immunoassay method according to claim 1, wherein the magnetic marker is optically detected.

3. The immunoassay method according to claim 1, wherein the magnetic marker is a handling agent that facilitates binding of a complex of the detection moiety and the target analyte to the solid substrate.

4. The immunoassay method according to claim 1, wherein the sample is a body fluid.

5. The immunoassay method according to claim 1, wherein the solid substrate has a shape of at least one of beads, strips, slides, and chips.

6. The immunoassay method according to claim 1, wherein the solid substrate comprises at least one material of latex, plastic, gold, silicon, silicon nitride, or glass.

7. The immunoassay method of claim 1, wherein the sample is a tissue sample.

8. The immunoassay method of claim 1, wherein the immunoassay method holds a sample volume of greater than or equal to 1 μL and less than or equal to 30 μL.

9. The immunoassay method of claim 1, wherein the presence or absence of NT-proBNP or BNP is detected in less than five minutes.

* * * * *